(12) United States Patent
Ogasawara et al.

(10) Patent No.: US 6,607,490 B2
(45) Date of Patent: Aug. 19, 2003

(54) ULTRASONIC DIAGNOSTIC APPARATUS AND CONTROL METHOD THEREOF

(75) Inventors: Yoichi Ogasawara, Nasu-gun (JP); Naohisa Kamiyama, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/050,958

(22) Filed: Jan. 22, 2002

(65) Prior Publication Data
US 2002/0165454 A1 Nov. 7, 2002

(30) Foreign Application Priority Data
Jan. 22, 2001 (JP) ..................... 2001-013563

(51) Int. Cl.$^7$ .............................. A61B 8/14
(52) U.S. Cl. .................................... 600/458
(58) Field of Search .................. 600/437, 440–458, 600/461–471, 459; 73/625, 626; 128/916; 367/7, 11, 130, 138; 424/9.51, 9.52

(56) References Cited

U.S. PATENT DOCUMENTS

| | | | |
|---|---|---|---|
| 5,694,937 A | | 12/1997 | Kamiyama |
| 5,833,613 A | | 11/1998 | Averkiou et al. |
| 5,860,931 A | * | 1/1999 | Chandler ..................... 600/458 |
| 5,971,928 A | * | 10/1999 | Dodd et al. ................. 600/458 |
| 6,015,384 A | * | 1/2000 | Ramamurthy et al. ...... 600/440 |
| 6,054,118 A | * | 4/2000 | .O slashed.stensen ...... 424/9.52 |
| 6,302,846 B1 | * | 10/2001 | Gardner ....................... 600/458 |
| 6,315,730 B1 | * | 11/2001 | Hoff et al. ................... 600/458 |

* cited by examiner

Primary Examiner—Marvin M. Lateef
Assistant Examiner—Ali M. Imam
(74) Attorney, Agent, or Firm—Oblon, Spivak, McClelland, Maier & Neustadt, P.C.

(57) ABSTRACT

(n-1) frames of image information which rarely includes contrast agent information are subtracted from addition information obtained by adding a multi-shot image group consisting of a plurality of frames (for example, n-1 frames) which includes the contrast agent information, thereby acquiring image information based on all of the contrast agent which has existed in one scanning plane in the image processing manner.

28 Claims, 9 Drawing Sheets

ULTRASONIC DIAGNOSTIC APPARATUS AND CONTROL METHOD THEREOF

CROSS-REFERENCE TO RELATED APPLICATIONS

This application is based upon and claims the benefit of priority from the prior Japanese Patent Application No. 2001-13563, filed Jan. 22, 2001, the entire contents of which are incorporated herein by reference.

BACKGROUND OF THE INVENTION

1. Field of the Invention

The present invention relates to an ultrasonic diagnostic apparatus capable of performing detection of blood flow perfusion and quantitative evaluation of the perfusion by using an ultrasonic contrast agent.

2. Description of the Related Art

An ultrasonic diagnostic apparatus can non-invasively obtain a tomogram image of a soft tissue in a living body from a body surface by an ultrasonic pulse reflection method, and has features that it is smaller in size and inexpensive, capable of real-time display, has high safety without exposure to, e.g., X rays and capable of blood flow imaging, as compared with any other diagnostic apparatus such as an X-ray diagnostic apparatus, an X-ray CT apparatus, an MRI diagnostic apparatus or a nuclear medicine diagnostic apparatus. The ultrasonic diagnostic apparatus is currently commonly used for hearts, abdominal parts, a urinary organs, and obstetrics and gynecology because of its conveniences mentioned above.

As one of radiography methods of the ultrasonic image diagnostic apparatus, there is a technique called contrast echo. This intensifies the ultrasonic scattering echo by injecting an ultrasonic contrast agent consisting of, e.g., micro-bubbles in a blood vessel of a patient. For example, in an examination of a heart or an abdominal organ, its purpose is to inject an ultrasonic contrast agent from a venation and intensify a blood flow signal in order to evaluate a blood flow dynamic state. In particular, in case of injecting the ultrasonic contrast agent into the venation, the invasiveness is low. Therefore, since the burden on a patient is lightened, the diagnosis based on this method of evaluating the blood flow dynamic state is getting popular.

Further, in recent years, an ultrasonic scanning sequence called intermittent transmission which makes use of the ultrasonic contrast agent has been developed and is outstanding successful in the clinical or study field. This intermittent transmission is a scanning sequence which waits until the ultrasonic contrast agent is sufficiently filled in a region of interest and then performs transmission of the ultrasonic waves. Furthermore, it destructs and dissolves the micro-bubbles at a blast in order to obtain the high signal intensity. Generally, in this intermittent transmission, it is ideal that one-frame scanning is carried out in accordance with each intermittent interval and the micro-bubbles filled in the cross section of a target are diminished and dissolved at a blast, thereby observing an area where the micro-bubbles have existed.

However, the micro-bubbles may not be diminished and dissolved sufficiently in one frame scanning depending on types or concentrations of the contrast agent or a transmission acoustic field in some cases. Moreover, when the concentration of the contrast agent is too high or the transmission acoustic pressure is too low, attenuation of the acoustic pressure by the micro-bubbles becomes large, and the intensity of a reflection signal at a deep part can not be satisfactorily obtained. Alternatively, even if the sufficient signal intensity is obtained, the S/N ratio may be very poor, a phenomenon which glooms an image, which is so-called shadowing, may occur. In such cases, since the distribution state of the micro-bubbles in the scanning cross section at a deep position is not perceived and a ratio of destruction of the micro-bubbles varies, appropriate quantitative evaluation can not be performed. In addition, if the micro-bubbles in the scanning cross section can not be once completely diminished, dynamic observation of the blood flow dynamic state also becomes difficult.

As means for avoiding this problem, there is a technique disclosed in, e.g., Jpn. Pat. Appln. KOKAI Publication No. 9-164138. This technique makes judgment upon at which depth information of bubbles of a patient is obtained based on an absolute value of a difference between frames calculated by using data acquired by transmission of strong ultrasonic waves and data acquired by transmission of weak ultrasonic waves. Additionally, based on this judgment, transmission and reception of ultrasonic waves in which a focusing point is automatically shifted from a shallow part to a deep part are repeated, and an obtained absolute value image is integrated and displayed.

In this technique, however, a number of times of transmission and reception of ultrasonic waves is usually twofold of a number of regular frames, and transmission/reception control or judging means may be possibly complicated. Further, since a number of frames is large, it takes time to collect data of all frames. Thus, a difference in time between an image of the frame collected at first and the frame collected at last becomes large, and the displacement of an image due to movement becomes prominent when creating an image of a moving target, thereby deteriorating the picture quality.

Meanwhile, for the purpose of completely destructing and dissolving the micro-bubbles, there is a technique which performs frame scanning for imaging several times after intermittence, which is so-called multi-shot. According to this multi-shot, a number of times of multi-shot to be required differ depending on types or concentrations of contrast agent or a transmission acoustic field. However, selecting appropriate conditions can makes the micro-bubbles in the scanning cross section diminished and dissolved at a high ratio by.

Incidentally, a point of notice is that multi-shot can insistently completely destruct the micro-bubbles contained in the cross section of an observation target and rest to an initial state with no micro-bubbles and it is not means for extracting information of the diminished micro-bubbles. That is, even if all the micro-bubbles are diminished by multi-shot, a frame image corresponding to each shot can not independently provide information of all the micro-bubbles in the cross section as an observation target. In this case, even if any frame is selected, an image whose brightness is irregular in the depth direction is generated, the correct distribution of the contrast agent can not be obtained. Also, in quantification measurement using the contrast agent, correct evaluation can not be obtained unless an evaluation area can be appropriately selected.

It is an object of the present invention to provide means capable of accurately and effectively performing detection of blood flow perfusion and its quantitative evaluation even if a quantity of a contrast agent to be injected is large or a concentration of the same is high.

BRIEF SUMMARY OF THE INVENTION

To achieve this aim, the present invention takes the following configurations.

According to a first aspect of the present invention, there is provided an ultrasonic diagnostic apparatus comprising: a transmission/reception device which transmits for a plurality of times ultrasonic waves having an intensity capable of destructing a contrast agent to one scanning plane of an object to which the contrast agent has been injected and receives a reflected wave group from the object; a data generator which generates a plurality of accumulative addition data having different time phases based on at least one of a plurality of reflected waves constituting a plurality of continuous frames in the reflected wave group and generates subtraction data from a reflected wave received from the object with a predetermined timing; and an image information generator which generates calculated data having an operation value to which a plurality of the accumulative addition data has been accumulatively added and from which the subtraction data has been subtracted, and generates ultrasonic wave image information concerning the scanning plane based on the calculated data.

According to a second aspect of the present invention, there is provided an ultrasonic diagnostic apparatus comprising: a transmission/reception device which transmits for a plurality of number of times ultrasonic waves having an intensity capable of destructing a contrast agent to one scanning plane of an object to which the contrast agent has been injected, and receives a reflected wave group from the object; a data generator which generates a plurality of accumulative addition data having respective time phases based on at least one of a plurality of reflected waves composing a plurality of continuous frames in the reflected wave group, and generates subtraction data from a reflected wave received from the object with a predetermined timing; a memory which stores therein a plurality of the accumulative addition data; and an image information generator which generates calculated data obtained by subtracting the subtraction data from each of the accumulative addition data stored in the memory, and generates ultrasonic image information concerning the scanning plane based on the calculated data.

According to a third aspect of the present invention, there is provided an ultrasonic diagnostic apparatus control method comprising: transmitting for a plurality of number of times ultrasonic waves having an intensity capable of destructing a contrast agent to one scanning plane of an object to which the contrast agent has been injected; receiving a reflected wave group from the object; generating a plurality of accumulative addition data having respective time phases based on at least one of a plurality of reflected waves composing a plurality of continuous frames in the reflected wave group; generating subtraction data from a reflected wave received from the object with a predetermined timing; generating calculated data having an operation value to which a plurality of the accumulative addition data have been added and from which the subtraction data has been subtracted; and generating ultrasonic image information concerning the scanning plane based on the calculated data.

According to a fourth aspect of the present invention, there is provided an ultrasonic diagnostic apparatus control method comprising: transmitting for a plurality of number of times ultrasonic waves having an intensity capable of destructing a contrast agent to one scanning plane of an object to which the contrast agent has been injected; receiving a reflected wave group from the object; generating a plurality of the accumulative addition data having different time phases based on at least one of a plurality of reflected waves composing a plurality of continuous frames in the reflected wave group; generating subtraction data from a reflected wave received from the object with a predetermined timing; generating calculated data obtained by subtracting the subtraction data from the each of accumulative addition data; and generating ultrasonic image information concerning the scanning plane based on the calculated data.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First to fifth embodiments according to the present invention will now be described with reference to the accompanying drawings. Incidentally, although the following will describe the case where an abnormal part is identified based on a blood flow state of an organ in an abdominal area, application of this ultrasonic diagnostic apparatus is not restricted this example. For instance, it can be applied to any other organ such as a heart or urinary organs. Further, like reference numerals denote constituent parts having substantially the same function and structure, and tautological explanation is given only when necessary.

<First Embodiment>

Figure 1:
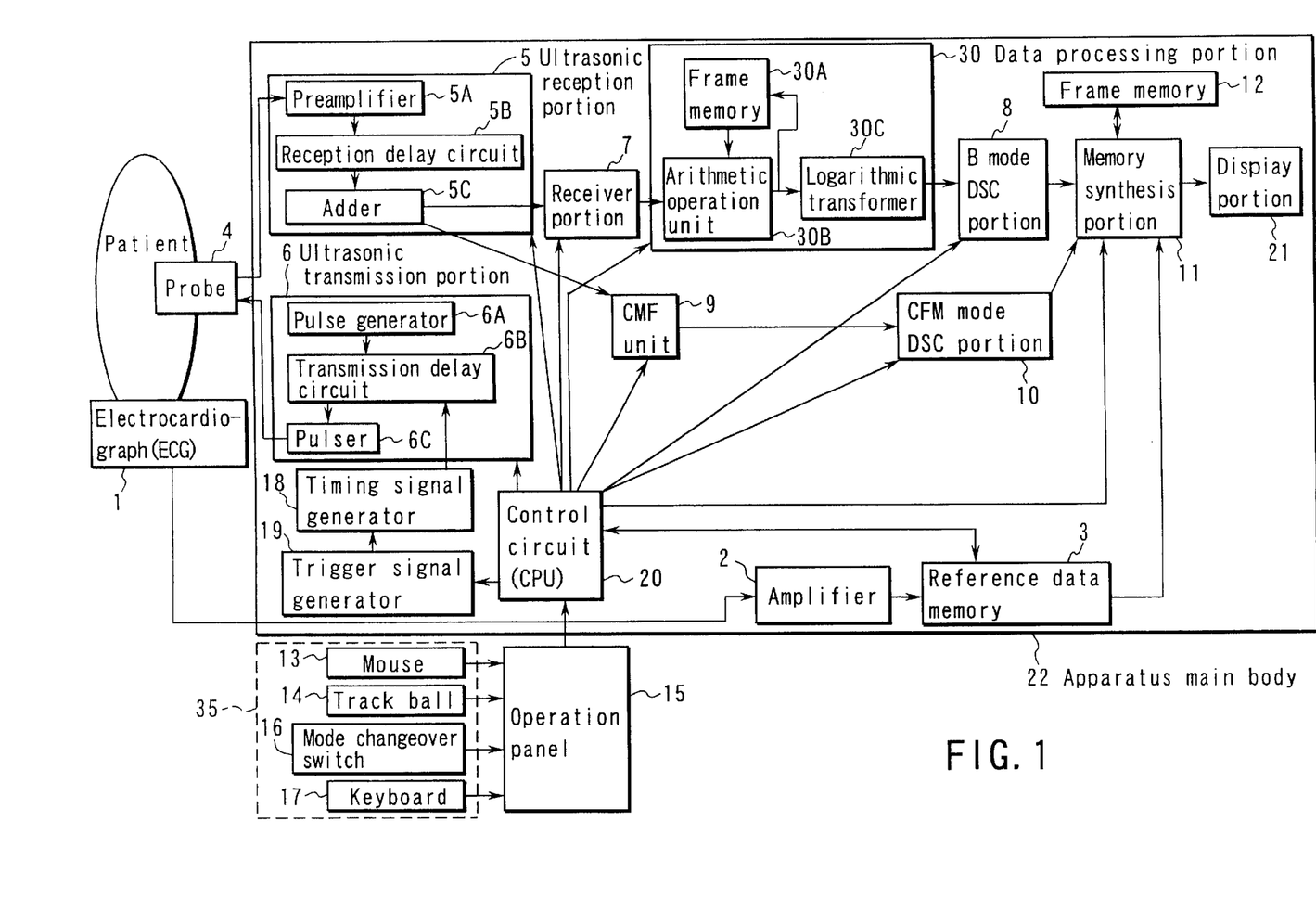
FIG. 1 is a block diagram showing an ultrasonic diagnostic apparatus according to an embodiment.

FIG. 1 is a block diagram showing an ultrasonic diagnostic apparatus according to this embodiment.

In FIG. 1, the ultrasonic diagnostic apparatus according to this embodiment is constituted by an electrocardiogram (ECG) 1, an ultrasonic probe 4, an apparatus main body 22, an operation panel 15, and an input device 35. Each constituent part will now be described hereunder.

(Electrocardiograph)

The electrocardiograph (ECG) 1 measures a graph on which a change in electrical phenomenon of a heart of a patient with time, i.e., an electrocardiogram. An electrocardiographic wave signal detected by the electrocardiograph 1 is transmitted to a reference data memory 3 through an amplifier 2, supplied to a display portion 21 through a memory synthesis portion 11 if necessary, and displayed as an electrocardiographic wave.

(Ultrasonic Probe)

The ultrasonic probe 4 has piezoelectric vibrators as acoustic/electrical reversible conversion elements such as piezoelectric ceramic. A plurality of the piezoelectric vibrators are aligned and provided at an end of the probe 4.

(Ultrasonic Diagnostic Apparatus Main Body)

The apparatus main body 22 has the amplifier 2, the reference memory data 3, an ultrasonic reception portion 5, an ultrasonic transmission portion 6, a receiver portion 7, a CFM unit 9, a data processing portion 30, a B mode DSC portion 8, a CFM mode DSC portion 10, the memory synthesis portion 11, a frame memory 12, a timing signal generation portion 18, a trigger signal generation portion 19, a control circuit (CPU) 20, and a display portion 21.

The ultrasonic transmission portion 6 has a pulse generator 6A, a transmission delay circuit 6B and a pulser 6C, and is connected to the probe 4.

The pulse generator 6A repeatedly generates a rate pulse at a rate frequency fr Hz (cycle; 1/fr second) of 5 kHz, for example. This rate pulse is split by a number of channels and transmitted to the transmission delay circuit 6B. The transmission delay circuit 6B converges the ultrasonic waves in the form of a beam, and gives the delay time required for determining the transmission directivity to each rate pulse. It is to be noted that a trigger from a trigger signal generator 19 is supplied to the transmission delay circuit 6B through a timing signal generator 18 as a timing signal. The pulser 6C applies a voltage pulse to the probe 4 in accordance with each channel with a timing of reception of the rate pulse from the transmission delay circuit 6B. As a result, the ultrasonic beam is transmitted to a patient.

A reflected wave which has been transmitted as described above and reflected on a discontinuous plane of the acoustic impedance in the patient is received by the probe. An echo signal outputted from the probe 4 for each channel is fetched to the ultrasonic reception portion 5.

The ultrasonic reception portion 5 has a preamplifier 5A, a reception delay circuit 5B and an adder 5C. The preamplifier 5A amplifies the echo signal fetched to the ultrasonic reception portion 5 through the probe 4 in accordance with each channel. The amplified echo signal is provided with the delay time required for determining the reception directivity from the reception delay circuit 5B, and added by the adder 5C. By this addition, a reflected component from a direction corresponding to the reception directivity of the echo signal is emphasized. Based on the reception directivity and the transmission directivity, the comprehensive directivity of the ultrasonic transmission/reception is determined. This directivity is generally referred to as a scanning line. The echo signal subjected to such a series of processing is transmitted from the ultrasonic reception portion 5 to the receiver portion 7 and a color flow mapping (CMF) unit 9.

Although not shown, the receiver portion 7 is constituted by an envelope detection circuit and an analog-to-digital converter (A/D) converter. The envelope detection circuit detects an envelope curve. The detected detection signal is digitized through the analog-to-digital converter, and outputted to a circuit on a rear stage as detection data.

Although not shown, the color flow mapping (CFM) unit 9 is constituted by a phase detection circuit, an analog-to-digital converter, an MTI filter, an auto-correlator and an arithmetic calculation portion. It extracts a blood flow component obtained by Doppler effect and acquires blood flow information such as an average speed, dispersion, power and others in multipoint. The blood flow information is supplied to a display portion 21 through the CFM mode DSC portion 10 and the memory synthesis portion 11, and displayed in color as an average speed image, a dispersion image, a power image and an image of combination of these images.

The control circuit (CPU) 20 performs control concerning the operation of the ultrasonic diagnostic apparatus, and control concerning the ultrasonic image diagnosis by the later-described intermittent transmission in particular as a control center of the entire system.

The data processing portion 30 is basically constituted by a frame memory 30A, an arithmetic operation unit 30B and a logarithmic transformer 30C. The detection data inputted to the data processing portion 30 is processed in units of frame (which will be referred to as frame data hereinafter). The frame data is inputted to the arithmetic operation unit 30B, and addition or subtraction processing between sets of frame data is carried out. The frame memory 30A has memory elements whose number equals to a number of scanning lines required to constitute a number of requested frames or equals to a number of samples on the scanning line, and stores therein frame data outputted from the arithmetic operation unit 30B. Further, the stored frame data is read from the frame memory 30A in accordance with control from the control circuit 20, and inputted to the arithmetic operation unit 30B, or a result of the finally calculated frame data is inputted to the logarithmic transformer 30C provided on an output stage. The logarithmic transformer 30C performs logarithmic compression of the calculated frame data inputted thereto, and transmits it to the display portion 21 through a B mode digital scanning converter (DSC) portion 8 and the memory synthesis portion 11. It is to be noted that the memory synthesis portion 11 carries out conversion processing from the scanning line signal string for ultrasonic scanning into a scanning line signal string having a general video format as typified by TV or the like. Furthermore, the memory synthesis portion 11 synthesizes one frame from character information of various kinds of setting parameters, graduation, a later-described guidance image and others, and outputs it as a video signal to the display portion 21.

In regard to arithmetic operation processing by the data processing portion 30, it is necessary to carry out arithmetic operation of a linear signal before logarithmic compression. In case of providing the logarithmic transformer to the receiver portion 7 and utilizing a signal subjected to logarithmic compression, however, it is good enough to set a logarithmic inverter to an input stage of the data processing portion 30, inverting the signal into a linear signal and performing the similar operation. This can be likewise applied to the case of setting the data processing portion before video format conversion processing at a rear stage of the B mode DSC portion 8 or in the memory synthesis portion 11.

The display portion 21 displays a spatial distribution of the contrast agent, namely, a blood flow image. The frame memory 12 is provided in order to store a digital data output from the memory synthesis portion 11.

(Operation Panel/Input Device)

The operation panel 15 is connected to the apparatus main body 22, and there is provided the input device 35 (for example, a mouse 13, a track ball 14, a mode changeover switch 16, a keyboard 17 or the like) used for, e.g., setting a region of interest (ROI) in order to fetch various kinds of instructions/commands/information from an operator into the apparatus main body 22.

Description will now be given as to the technical background of the ultrasonic diagnostic apparatus for better understanding of its function.

Generally, micro-bubbles are a source of reflection for most of contrast agents. The contrast effect becomes higher as a quantity or a concentration of a contrast agent to be injected is larger. Further, the bubbles are diminished and dissolved in a very short time by irradiation of the ultrasonic waves because of their property. Therefore, the contract medium effective time is shortened by irradiation of the ultrasonic waves.

On the other hand, it is known that the micro-bubbles of the contrast agent acoustically provoke a non-linear phenomenon by irradiation of the ultrasonic waves and include a second harmonic (harmonics) component of a transmission frequency. This harmonics component is generated even in a soft tissue of a living body in the process of ultrasonic propagation. In particular, when the micro-bubbles are diminished and dissolved, the very large harmonics component is generated, and a contrast difference can be hence relatively given to a soft tissue of a living body having a small harmonics component. That is, when the reflected echo includes a basic frequency component of transmitted ultrasonic waves and a harmonics component, the harmonics component is extracted by a filter, and a B mode image is generated and displayed based on the harmonics component. As a result a part where the contrast agent exists, namely, a flood flow part can be emphasized and imaged.

Furthermore, when irradiation of the ultrasonic waves is performed by multi-shot in order to destruct and dissolve the micro-bubbles of the contrast agent, information of all micro-bubbles is not included in the cross section obtained by a first shot in an area where the micro-bubbles exist or an evaluation area for quantitative evaluation which should be finally imaged, and inclusion of this information depends on conditions such as a concentration of the contrast agent or a transmission acoustic pressure as described above.

However, an image for each shot obtained by each multi-shot has information of the second harmonic waves of the micro-bubbles which have not been diminished and dissolved by the previous shot and information of the second harmonic waves from a soft tissue of a living body. That is, a total quantity of the echo signals from the micro-bubbles which have existed in the scanning plane during a time of execution of multi-shot includes all of image information based on all of the contrast agent which has existed in the scanning plane. A total quantity of the echo signal can be calculated based on integration information of images obtained by each multi-shot.

Thus, the present ultrasonic diagnostic apparatus proposes a technical idea for obtaining an ultrasonic image of a soft tissue of a living body which can provide the high quantitative evaluation with the excellent repeatability and the good accuracy based on a total quantity of the echo signal from the micro-bubbles which have existed in the scanning plane during execution of the multi-shot. Specifically, (n−1) shots of image information which hardly includes contrast agent information is subtracted from addition information obtained by adding a group of a plurality of multi-shot images (for example, n−1 images. It is to be noted that n is a number of multi-shots) including the contrast agent information. Alternatively, the apparatus may be configure to add each of contrast agent information extracted by subtracting the image information which hardly includes the contrast agent information from each image including the contrast agent information.

Each image including the contrast agent information includes information from both the contrast agent echo and the tissue echo. On the other hand, the image information which hardly includes the contrast agent information consists of substantially only the tissue echo. It is, therefore, possible to acquire the image information based on all of the contrast agent which has existed in the scanning plane in the image processing manner.

(Operation)

Ultrasonic image acquisition processing executed by the present ultrasonic diagnostic apparatus will now be described.

Figure 2A:
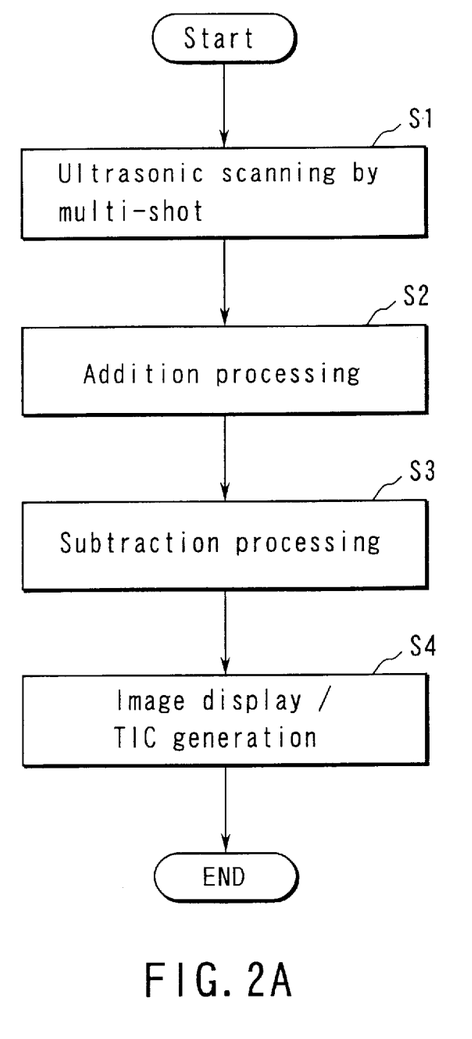
FIGS. 2A and 2B are flowcharts showing a flow of ultrasonic image acquisition processing executed by the ultrasonic diagnostic apparatus.

FIG. 2A is a flowchart showing a flow of ultrasonic image acquisition processing executed by the present ultrasonic diagnostic apparatus. Based on this drawing, there will be described an embodiment that frame data which is the (n−1)-th from the first input is accumulatively added, the n-th frame data is subtracted by a number of added shots, namely, the n-th frame data is subtracted by (n−1)-fold, and only a part of the contrast agent is extracted and superposed on one set of frame data.

(Ultrasonic Scanning by Multi-Shot: Step S1)

Intermittent transmission (flash echo) with a number of multi-shots being determined as n is carried out with respect to a patient to which the contrast agent has been injected. In this intermittent transmission, ultrasonic wave irradiation for the purpose of destructing and dissolving the micro-bubbles and ultrasonic wave irradiation for the purpose of only monitoring a diagnosis target without destructing and dissolving the micro-bubbles are intermittently executed. The radiography conformation by the latter ultrasonic irradiation, namely, the radiography conformation which monitors a diagnosis target by transmitting at desired time intervals ultrasonic waves with a relatively low acoustic pressure by which micro-bubbles are not diminished and dissolved after injecting the contrast agent is called a monitor mode.

Figure 3A:
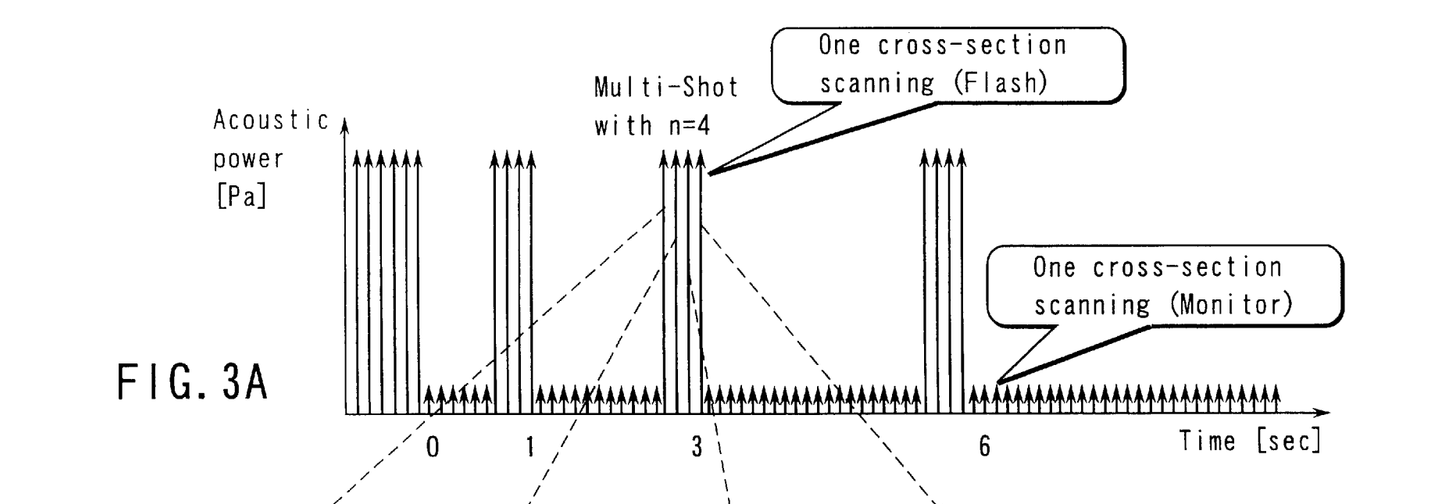
FIG. 3A is a view showing an example of a scanning sequence of intermittent transmission when n=4, and FIG. 3B typically shows image information obtained by each scanning in one multi-shot when n=4.

FIG. 3A is a view showing an example of a scanning sequence of intermittent transmission when n=4. In the drawing, a horizontal axis represents a time during frame scanning, and a vertical axis represents a transmission acoustic pressure. Therefore, a length of each arrow reflects a transmission intensity of an acoustic pressure, and one arrow corresponds to irradiation of ultrasonic waves for one time. Irradiation indicated by a long arrow in the drawing corresponds to a flash echo, and irradiation indicated by a short arrow corresponds to a monitor mode.

According to this scanning sequence, the micro-bubbles are reserved in a target organ during each monitor mode. Then, at the end of the monitor mode (that is, when the micro-bubbles are sufficiently reserved in a target organ), scanning is performed with respect to an internal organ as a target with a relative high acoustic pressure such that the micro-bubbles are diminished and dissolved at a blast. It is to be noted that the intermittent transmission time interval may be an absolute time or may be determined based on the electrocardiograph. For example, in case of utilizing the electrocardiograph, there can be considered a structure which executes intermittent transmission with an obtained electrocardiographic wave signal as a trigger.

Here, a number of multi-shots n will now be described.

The ultrasonic diagnostic apparatus is configured to subtract (n−1) shots of the image information which rarely includes the contrast agent information from the addition information obtained by adding a plurality of shots (for example, n−1) of a multi-shot image groups including the contrast agent information, as described above. Therefore, a number of multi-shots n must be a number of times which can obtain at least one frame of the image information which rarely includes the contrast image information.

Figure 3B:
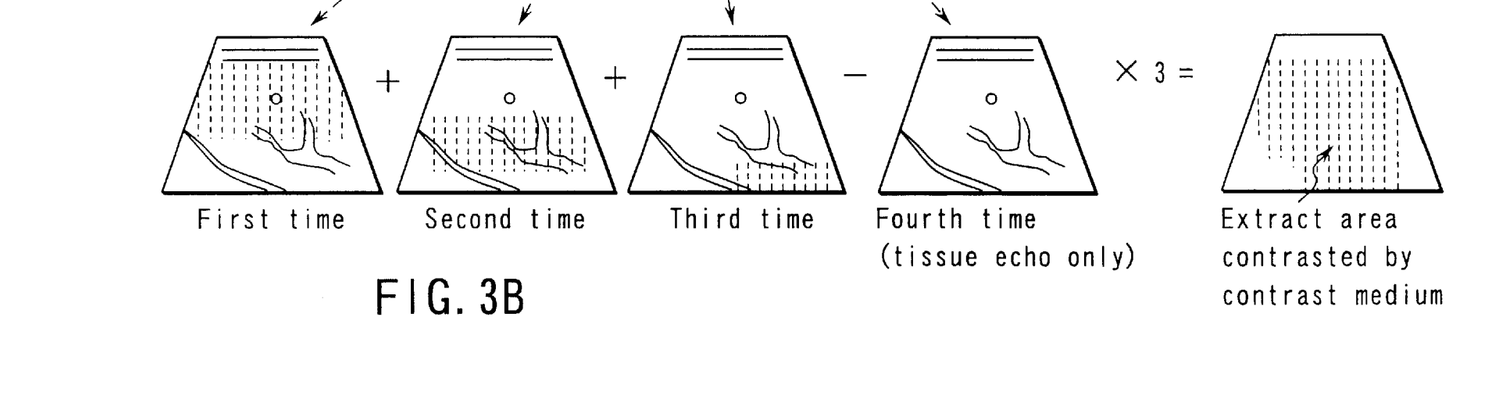

FIG. 3B typically shows the image information obtained by each scanning in the multi-shot when n=4. As described above, the image obtained by four times of scanning rarely includes the contrast image information.

The frame data based on the multi-shot is sequentially outputted from the receiver portion 7 and then inputted to the data processing portion 30.

(Addition Processing: Step S2)

Subsequently, addition processing is applied to (n−1) shots of the multi-shot image group including the contrast agent information. In the arithmetic operation unit 30B (see FIG. 1) in the data processing portion 30, the addition processing is executed as follows, for example. It is to be noted that the data inputted to the arithmetic operation unit 30B is the frame data from the receiver portion 7 and the frame data from the frame memory 30A, but input of these data and the operation of the arithmetic operation unit 30B are controlled by the control circuit 20.

When the frame data of the first shot obtained by the multi-shot is first inputted to the arithmetic operation unit 30B, the frame data passes through the arithmetic operation unit 30B without stopping or bypasses the same and stored in the frame memory 30A.

Then, in synchronization with input of a second shot of the frame data to the arithmetic operation unit 30B, the frame data of the first shot is called from the frame memory 30A and inputted to the arithmetic operation unit 30B. The arithmetic operation unit 30B adds and outputs the frame data sets of the first and second shots. The outputted and added frame data sets of the first and second shots are stored in the frame memory 30A.

Thereafter, the frame data sets of the third, fourth, ..., and (n−1)th shots are accumulatively added in the arithmetic operation unit 30B, and the accumulatively added the frame data sets of the (n−1) shots corresponding to irradiation from the first time to the (n−1)th time are stored in the frame memory 30A.

(Subtraction Processing: Step S3)

Subsequently, subtraction processing for subtracting (n−1) shots of the image information which rarely includes the contrast agent information is performed to the added frame data. This addition processing is executed in the arithmetic operation unit 30B in the data processing portion 30 as follows, for example.

When the frame data of the n-th shot is inputted to the arithmetic operation unit 30B after the frame data of the (n−1)th shot, the accumulatively added first to (n−1)th frame data is read from the frame memory and inputted to the arithmetic operation unit 30B.

The arithmetic operation unit 30B executes subtraction of (n−1)-fold of the n-th frame data, i.e., the (n−1) shots which are added until the n-th frame data is inputted from the accumulatively added first to (n−1)th frame data.

(Processing After Subtraction: Step S4)

The frame data finally outputted from the arithmetic operation unit 30B is subjected to logarithmic transformation in the logarithmic transformer 30C as described above and then supplied to the display portion 21 through the B mode digital scanning converter (DSC) portion 8 and the memory synthesis portion 11. In this manner, an ultrasonic image obtained by extracting information of the contrast agent is displayed.

(Generation of TIC: Step S4)

An output from the memory synthesis portion 11 is stored in the frame memory 12, and can be utilized for TIC (Time Intensity Curve) and any other measurement. This TIC is generated based on an average value of the intensity in ROI of each image, for example. Incidentally, the hardware structure is not restricted to the above-described conformation, and a structure which can produce similar outputs can be a target.

The finally obtained frame data can extract only information of the micro-bubbles which are diminished and dissolved by irradiation of ultrasonic waves for the first time to the (n−1)th time and can be superposed as the frame data of one shot (see FIG. 3B. However, n=4 in this drawing). As a result, imaging of an area where the contrast agent exists and the highly accurate quantitative evaluation become possible.

(Processing With Respect to Shadowing)

Incidentally, in cases where a target frame brings about shadowing, when the image of the n-th shot is simply subtracted, a harmonic component obtained from a soft tissue of a living body of the latter n-th shot is subtracted from a shadowing part of the former frame, namely, a signal of a non-signal portion. Therefore, a final image may show a negative value in some cases. It is possible to deal with such a case by adding absolute value processing or non-linear processing such as substituting a value equal to or below a given threshold value by a specific value such as zero in the arithmetic operation circuit 30B.

As described above, the ultrasonic diagnostic apparatus is configured to obtain an ultrasonic image having each contrast agent information by subtracting (n−1) shots of the image information which rarely includes the contract medium information from the addition information obtained by adding the multi-shot image group of a plurality of shots (for example, n−1 shots) including the contrast agent information. Alternatively, the ultrasonic diagnostic apparatus is configured to obtain the ultrasonic image having each ultrasonic medium information by adding each contrast agent information extracted by subtracting the image information which rarely includes the contrast agent information from each image including the contrast agent information.

Each image including the contrast agent information contains information from both the contrast agent echo and the tissue echo. On the other hand, the image information which rarely includes the contrast agent information contains substantially only information from the tissue echo. Therefore, the image information based on all of the contrast agent which has existed in the scanning plane can be obtained in the image processing manner. As a result, even if a quantity of the contrast agent injected is large or a concentration of the same is high, detection of the blood flow perfusion or quantitative evaluation of that perfusion can be accurately and effectively performed. Furthermore, since the image is generated from the collected data having a relatively small number of frames, it is possible to obtain an excellent image having relatively few artifacts.

<Second Embodiment>

A second embodiment according to the present invention will now be described. The second embodiment is an example which is effective for occurrence of shadowing in particular. An important point of the second embodiment is an idea of specifying a part where shadowing occurs by using a signal value after the subtraction processing described in connection with the first embodiment. Specifically, the following content is given.

A schematic structure of an ultrasonic diagnostic apparatus according to the second embodiment will be first explained. The structure of the ultrasonic diagnostic apparatus according to this embodiment is substantially the same as that of the ultrasonic diagnostic apparatus shown in FIG. 1 except the data processing portion 30. Accordingly, only the structure of the data processing portion 30 will be described in detail.

Figure 5:
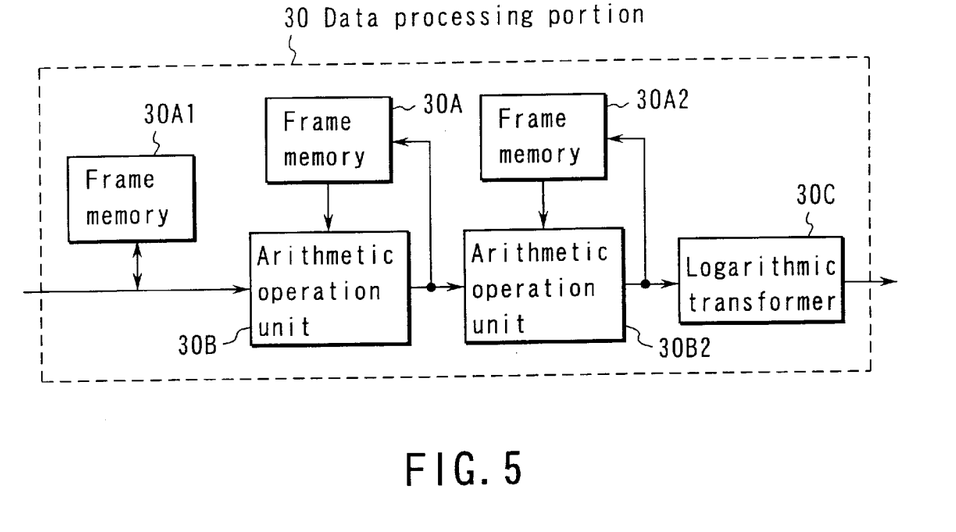
FIG. 5 is a view illustrating a structure of a data processing portion 30 that an ultrasonic diagnostic apparatus according to a second embodiment has.

FIG. 5 is a view illustrating the structure of the data processing portion 30 that the ultrasonic diagnostic apparatus according to this embodiment has.

As shown in FIG. 5, the data processing portion 30 newly has frame memories 30A1 and 30A2 and an arithmetic operation unit 30B2. The frame memory 30A1 is provided at a front stage of the arithmetic operation unit 30B, and the frame memory 30A2 and the arithmetic operation unit 30B2 are provided at a rear stage of the arithmetic operation unit 30B.

Figure 2B:
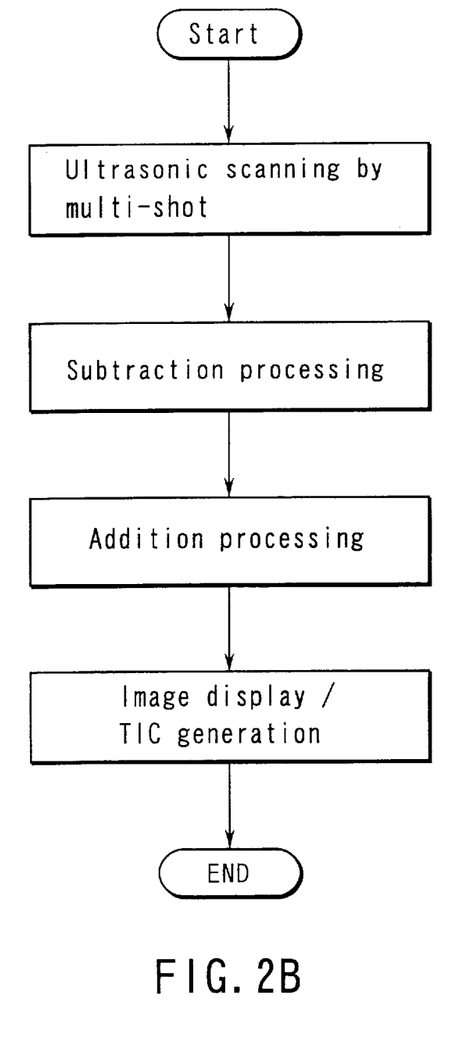

Description will now be given as to ultrasonic image acquisition processing executed by the ultrasonic diagnostic apparatus with reference to FIG. 2B. FIG. 2B is a flowchart showing a flow of the ultrasonic image acquisition processing executed by the ultrasonic diagnostic apparatus.

(Ultrasonic Scanning by Multi-Shot: Step S1)

At first, intermittent transmission with a number of multi-shots being determined as n is carried out to a patient after administration of the contrast agent. Its content is similar to that of the first embodiment.

(Subtraction Processing: Step S2)

Subtraction processing is then carried out with respect to the multi-shot image group of (n−1) shots including the contrast agent information in accordance with the following procedure.

For a start, the first frame data obtained by the multi-shot is outputted from the receiver portion 7 and inputted to the arithmetic operation unit 30B. Then, the frame data passes through the arithmetic operation unit 30B without stopping or bypasses the same and is stored in the frame memory 30A.

Subsequently, the second frame data also passes through the arithmetic operation unit 30B without stopping or bypasses the same and is stored in the frame memory 30A, as similar to the first frame data. Thereafter, the next to (n−1)th frame data sets pass through the arithmetic operation unit 30B and are stored in the frame memory 30A.

Then, the n-th frame data outputted from the receiver portion 7 is inputted to the arithmetic operation unit 30B but, on the other hand, it is stored in the frame memory 30A1. Moreover, in synchronization with input of the n-th frame data to the arithmetic operation unit 30B, the first frame data is read from the frame memory 30A and inputted to the arithmetic operation unit 30B.

In the arithmetic operation unit B, the n-th frame data is subtracted from the first frame data read from the frame memory 30A, and a negative value is substituted by zero. As a result, even if shadowing is presented in the first frame data, an area of shadowing does not become a negative value, and only the signal indicative of the micro-bubbles is extracted. A result of the arithmetic operation with respect to the first frame data passes through the arithmetic operation unit 30B2 without stopping and is stored in the frame memory 30A2.

Then, the n-th frame data stored in the frame memory 30A1 is read and inputted to the arithmetic operation unit 30B. In synchronization with this input, the second frame data stored in the frame memory 30A is read and inputted to the arithmetic operation unit 30B.

(Addition Processing: Step S3)

Subsequently, processing for extracting information of the contrast agent is executed with respect to he added frame data and subtraction processing for subtracting (n−1) shots of the image information which rarely includes the contrast agent information is carried out in the following manner, for example.

As described above, as similar to the first frame data operation, the n-th frame data is subtracted from the second frame data, and a negative value is substituted by zero. A result of this arithmetic operation is outputted to the arithmetic operation unit 30B2. In synchronization with input to the arithmetic operation unit 30B2, the frame data for the first time calculated by the arithmetic operation unit 30B is read from the frame memory 30A2 and inputted to the arithmetic operation unit 30B2. The arithmetic operation unit 30B2 adds the frame data for the first time calculated by the arithmetic operation unit 30B and the second frame data, and freshly stores them in the frame memory 30A2. Thereafter, similarly, subtraction of the third, fourth, . . . , and (n−1)th frame data and the n-th frame data and substitution of a negative value by zero are carried out in the arithmetic operation unit 30B, and then results are sequentially inputted to the arithmetic operation unit 30B2. In the arithmetic operation unit 30B2, addition is carried out before one frame in accordance with input of the frame data calculated by the arithmetic operation unit 30B, and the frame data stored in the frame memory 30B2 is read and accumulatively added at any time.

The frame data finally outputted from the arithmetic operation unit 30B is subjected to logarithmic transformation by the logarithmic transformer 30C as described above, and it is then supplied to the display portion 21 through the B mode digital scanning converter (DSC) portion 8 and the memory synthesis portion 11. In this manner, an ultrasonic image is displayed.

Figure 4:
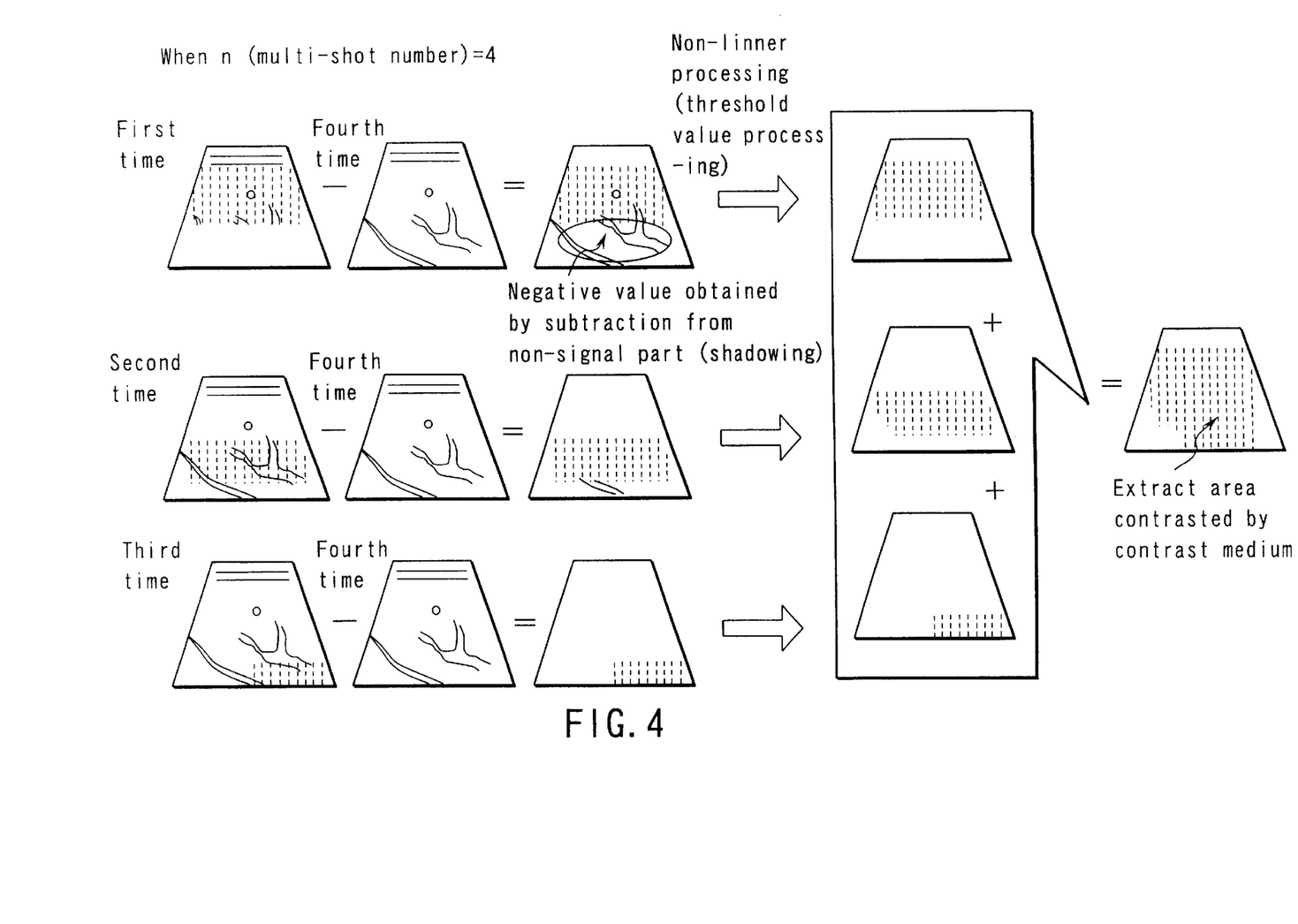
FIG. 4 is a view typically showing the image acquisition processing in the multi-shot when n=4.

FIG. 4 is a view typically showing the above-described image acquisition processing in the multi-shot when n=4. As shown in the drawing, threshold value processing is executed with respect to a signal value which becomes negative by subtracting an image which hardly includes the contrast agent information from the images of the first to third shots containing the contrast agent information (arrow in the drawing). After this threshold value processing, an area contrasted by the contrast agent can be extracted by adding each image.

(Generation of TIC: Step S4)

In addition, an output from the memory synthesis portion 11 is stored in the frame memory 12 and can be utilized for TIC (Time Intensity Curve) measurement or any other measurement. Incidentally, the hardware structure is not restricted to the above-described conformation, and a structure capable of producing similar outputs can be a target.

According to the structure mentioned above, when the n-th frame data is subtracted from each of the first to the (n−1)th frame data sets and a signal value becomes a negative value after this subtraction, there is executed processing for adding non-linear processing which substitutes this signal value by zero or takes an absolute value, for example. Thus, even if the image information is affected by shadowing for each frame, the contrast agent information can be extracted with the high extraction efficiency.

Third Embodiment

In general, in case of the pressure-resistant micro-bubble which may have a shell depending on types of contrast agents or of a high concentration, the micro-bubbles may not be efficiently diminished or dissolved with the multi-shot for n times in some cases.

The third embodiment shows an example capable of dealing with such a case. Specifically, it is an example of the ultrasonic diagnostic apparatus which can provide video information desired by an operator. For example, the apparatus is configured to display placing emphasis on information of the micro-bubbles in a specific frame such as a first frame or a second frame, or use addition information or subtraction information between specific frames.

Figure 6:
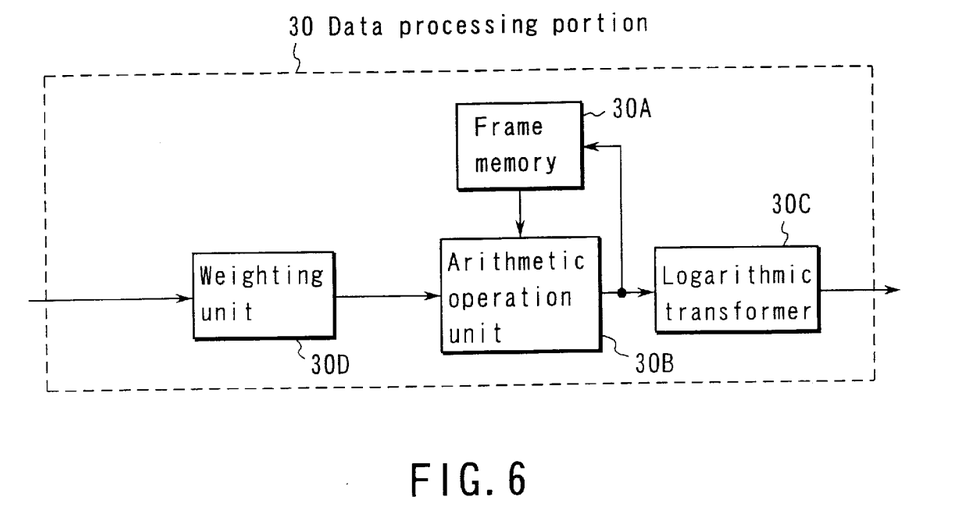
FIG. 6 is a view illustrating a structure of a data processing portion 30 that an ultrasonic diagnostic apparatus according to a third embodiment has.

FIG. 6 is a view showing a schematic structure of the ultrasonic diagnostic apparatus according to the third embodiment.

A characteristic point of this ultrasonic diagnostic apparatus lies in that a weighting unit 30D is provided at a front stage of the arithmetic operation unit 30B as shown in FIG. 6, for example. It is possible to perform image processing which places emphasis on information of the micro-bubbles in a specific frame by weighting executed by the weighting unit 30D.

The operation of the ultrasonic diagnostic apparatus according to this embodiment will now be described.

In FIG. 6, the weighting unit 30D has a function to select a value from values inputted from the operation panel 15 or values obtained by reading those written in an electronic file stored in a hard disk, a CD, an MO, an FD or a DVD provided in the apparatus main body, or a select a value provided from a storage medium mounted inside/outside the apparatus, such as a value obtained from a ROM mounted on a board of the apparatus, and to perform weighting by multiplying the selected value by a frame data from the receiver portion 7.

The weighted frame data is outputted from the weighting unit 30D and inputted to the arithmetic operation unit 30B. Thereafter, the similar operation as that in the first conformation is carried out, and a frame data group outputted from the receiver portion 7 is weighted by the weighting unit 30D of the data processing portion 30, subjected to addition or subtraction processing between frame data sets by the arithmetic operation unit 30B and stored in an arbitrary frame memory 30A. However, a difference from the first conformation is that weighting from, e.g., the second time to the (n−1)th time is determined as zero since an arbitrary weighting coefficient is given to an arbitrary frame, a weighting value for the first time and the n-th time is determined as 1 and subtraction processing is carried out in the arithmetic operation unit 30B. As a result, information of difference between specific frames, i.e., the first frame and the n-th frame can be obtained. It is to be noted that the weighting coefficient of a frame to be subtracted is equal to a sum of the weighting coefficients of the added frames in principle. Subtraction is carried out for the purpose of eliminating the harmonic component of a tissue.

Figure 7:
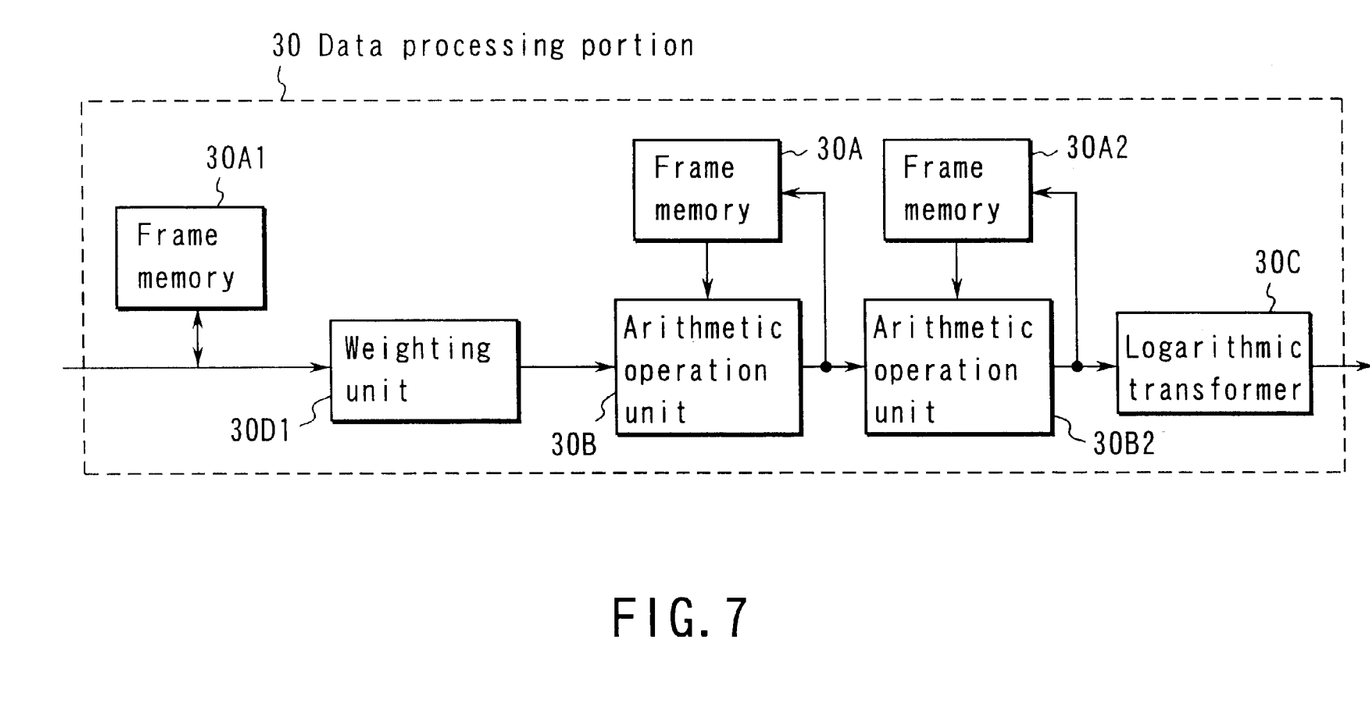
FIG. 7 is a view illustrating a modification of the structure of the data processing portion 30 that the ultrasonic diagnostic apparatus according to the third embodiment has.
Figure 8:
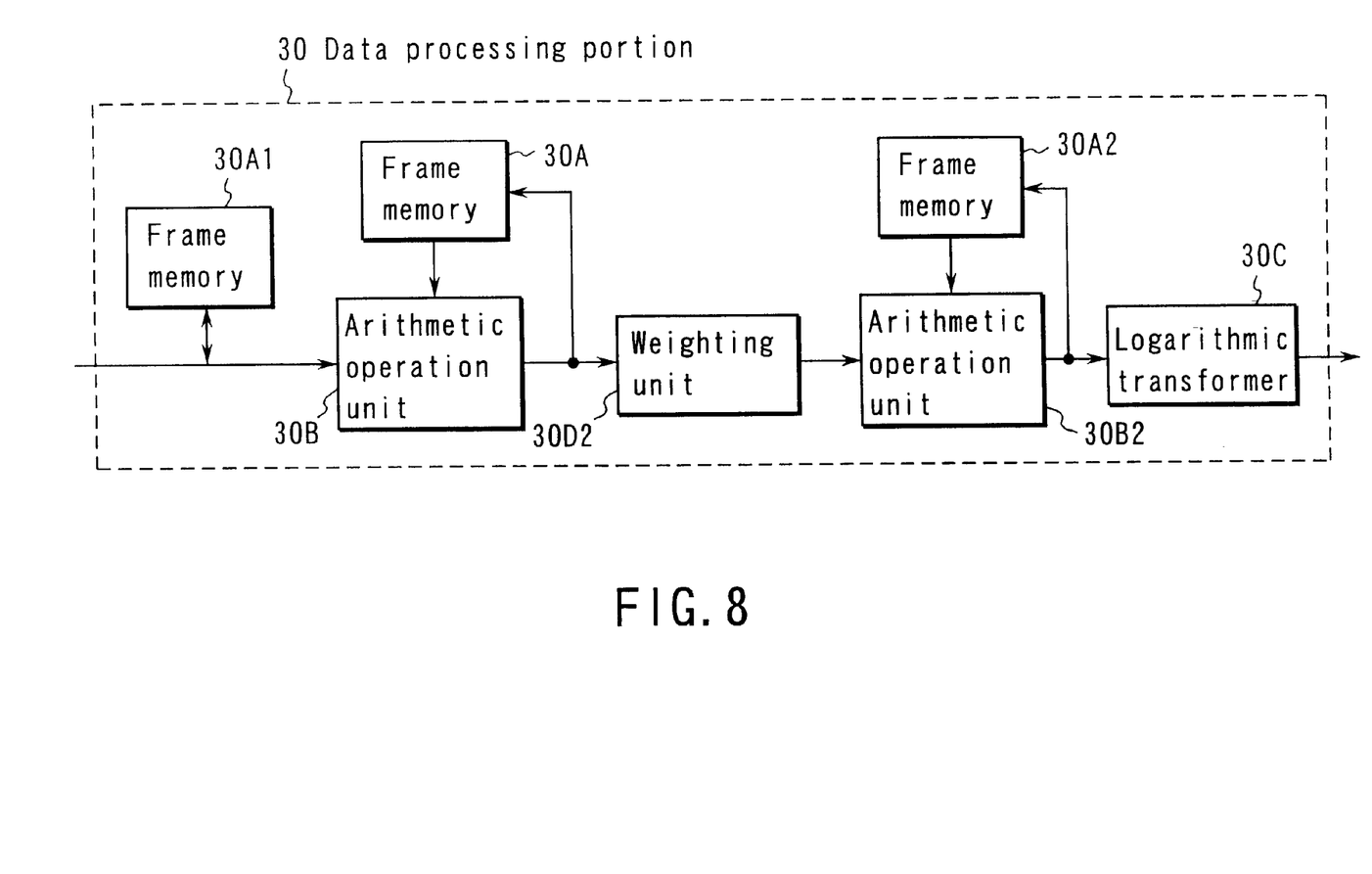
FIG. 8 is a view illustrating a modification of the structure of the data processing portion 30 that the ultrasonic diagnostic apparatus according to the third embodiment has.
Figure 9:
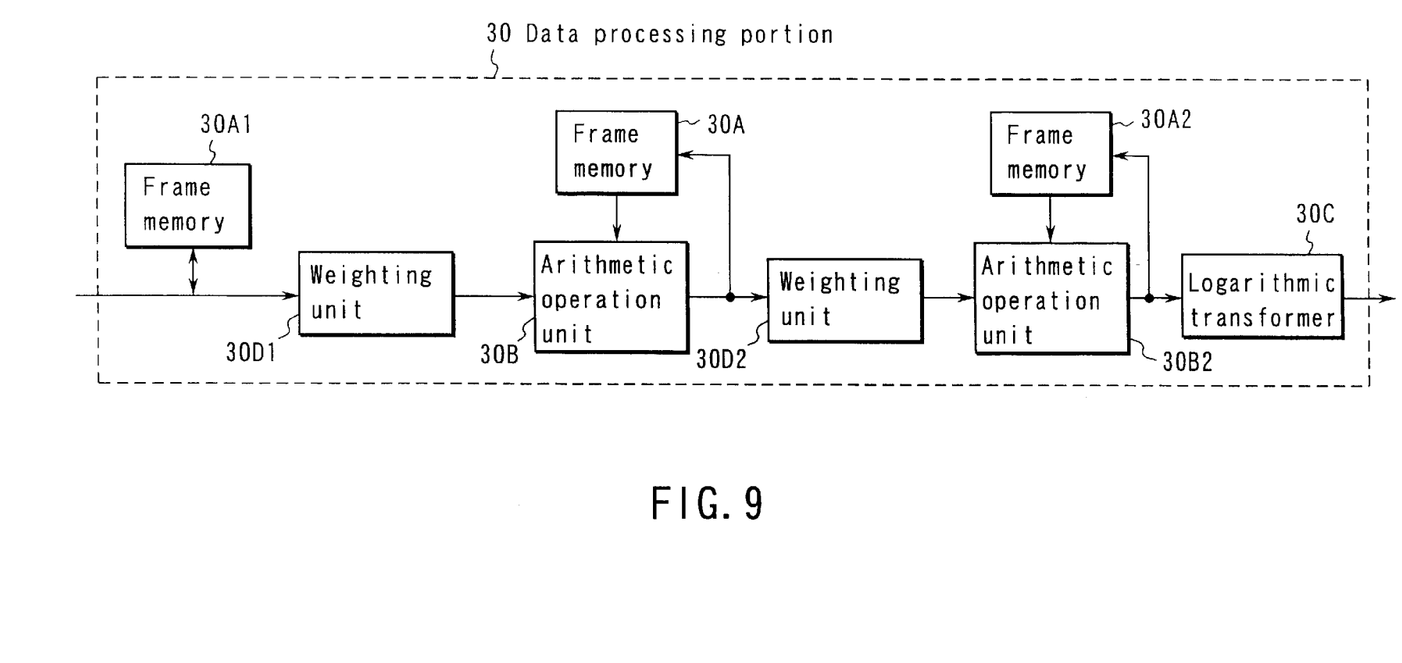
FIG. 9 is a view illustrating a modification of the structure of the data processing portion 30 that the ultrasonic diagnostic apparatus according to the third embodiment has.

Incidentally, the hardware structure is not restricted to the above-described conformation, and a structure capable of producing similar outputs can be a target. For example, as a modification of this embodiment, it is possible to adopt the structure in which the weighting unit 30D1 is set at a front stage of the arithmetic operation unit 30B with respect to the second conformation, as shown in FIG. 7. Additionally, it is possible to employ a structure in which the weighting unit 30D2 is set at a front stage of the arithmetic operation unit 30B2 with respect to the second conformation, as shown in FIG. 8. Further, as shown in FIG. 9, both the weighting units 30D1 and 30D2 can be set with respect to the second conformation.

Incidentally, although description has been given as to the case where several frame memories or weighting units are dispersed as an operation example, they may be physically collected as one element. Furthermore, the hardware structure is not restricted to the above-described conformation, and a structure capable of producing similar outputs can be a target.

Moreover, the above-described content is an example presuming use of all the frames. On the other hand, in order to visualize only a specific deep part contrasted by the contrast agent, only the second and subsequent frame data sets may be utilized without using, for example, the first frame in the obtained multi-shot.

Fourth Embodiment

The fourth embodiment will now be described.

In the third embodiment, the structure using hardware has been described as means for performing weighting processing. On the other hand, in the fourth embodiment, description will be given as to a structure which utilizes a host CPU or a single board computer and use data stored in the frame memory, thereby realizing the weighting processing by software. With the structure using software, inter-data processing of the frame data obtained from the multi-shot by an operator can be freely defined and realized.

For example, the weighting processing described in connection with the third embodiment can be represented by the following expression.

With respect to the first embodiment, assuming that the i-th ($1 \leq i \leq n$) of the multi-shot is $F_i$; a weighting value with respect to the frame data $F_i$ is $\alpha_i$; a weighting value concerning $F_i$ of the frame data $F_n$ is $\alpha_{n,i}$; an absolute value function is abs( ); a function which converts a value not more than a threshold value a into b is conv[a, b]( ); a sign indicative of addition between frame data sets is +; and a sign for multiplying frame data by a scalar quantity is *, the weighting processing can be represented by the following expression:

$$\sum_{i=1}^{n} \alpha_i * F_i$$

(where $\alpha_i$ is an actual number)

Furthermore, with respect to the second embodiment, the weighting processing can be expressed as follows:

$$\sum_{i=1}^{n-1} abs(\alpha_i * F_i + \alpha_{n,i} * F_i) \text{ or } \sum_{i=1}^{n-1} conv[0, 0](\alpha_i * F_i + \alpha_{n,i} * F_i)$$

(where $\alpha_{n,i}$ is an actual number)

As described above, this embodiment has a function which can define several functions, program an image demanded by an operator from an operation panel such as the keyboard 17 and provide it.

Fifth Embodiment

A fifth embodiment will now be described with reference to FIGS. 3 and 10. The ultrasonic diagnostic apparatus according to the fifth embodiment controls transmission conditions so that a focusing point of each ultrasonic wave to be transmitted becomes gradually deeper in the multi-shot executed in the first to fourth embodiments. Consequently, the contrast agent can be efficiently diminished from the surface of a patient toward the inside of the same, and effective image information can be efficiently taken out.

Figure 10:
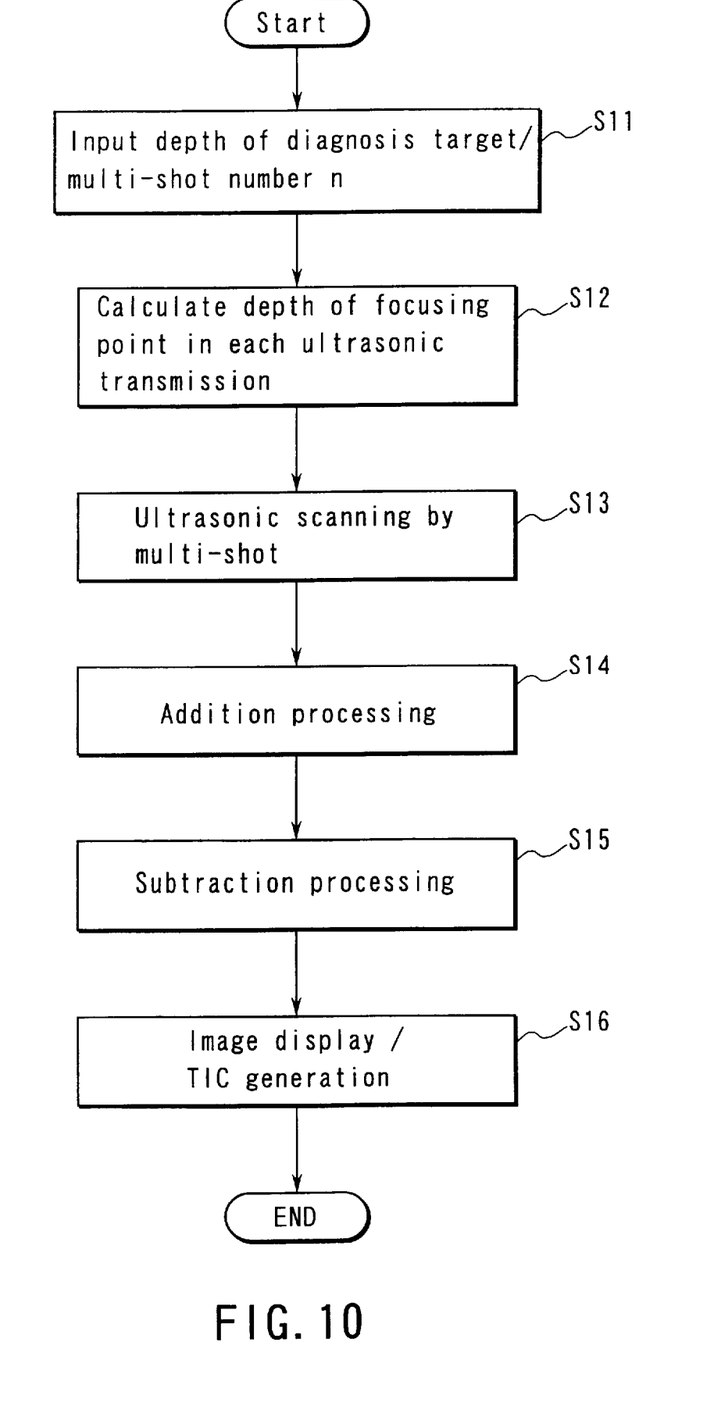
FIG. 10 is a flowchart showing a flow of ultrasonic image acquisition processing carried out by an ultrasonic diagnostic apparatus according to a fifth embodiment has.

FIG. 10 is a flowchart showing a flow of ultrasonic image acquisition processing carried out by the ultrasonic diagnostic apparatus according to this embodiment. In FIG. 10, a depth of a diagnosis target and a number of times of multi-shot n are inputted (step S11). In order to give concrete description, a number of times of multi-shot inputted at the step S11 is determined as n=4 in accordance with the scanning sequence example shown in FIG. 3.

A focusing depth in each ultrasonic transmission in multi-shot is then calculated (step S12). That is, in FIG. 3, in regard to ultrasonic transmission (in the current case, the fourth ultrasonic transmission) which includes reflected waves from only the tissue echo and is used for the above-described subtraction processing, a focusing depth is set at or in the vicinity of a diagnosis target. At this moment, when the focusing depth is set slightly deeper than the diagnosis target, the contrast agent which exists in the diagnosis target can be efficiently diminished.

Moreover, as to unperformed ultrasonic transmission (in the current case, the first to third times), the focusing depth is set at equal intervals so that focusing gradually becomes deeper. That is, a distance L is obtained by dividing a distance from the focusing depth set at the diagnosis target to a predetermined reference position (for example, the surface of a patient) by a number of times of remaining transmission. Then, the focusing depth of the first ultrasonic transmission is set at a position of the depth L from the surface of the patient; the focusing depth of the second ultrasonic transmission, a position of the depth 2L from the surface of the patient; and the focusing depth of the third ultrasonic transmission, a position of the depth 3L from the surface of the patient, respectively.

Subsequently, ultrasonic scanning by multi-shot is executed while controlling an ultrasonic beam opening width in such a manner that the focusing point moves to the position set in each ultrasonic transmission (step S13). Incidentally, control over the opening width is executed by the ultrasonic transmission portion 6.

Then, by executing the addition processing (step S14), the subtraction processing (step S15) and image display/TIC measurement (step S16) with the above-described contents, it is possible to obtain the ultrasonic image in which only the micro-bubbles which have been diminished and dissolved in ultrasonic transmission for the first to third times are extracted. It is to be noted that the processing order of the steps S13 and S14 can be counterchanged in accordance with the second embodiment.

According to the structure mentioned above, the contrast agent can be efficiently diminished from the surface of a patient towards the inside of the same, and the effective image information can be efficiently taken out, thereby contributing to highly accurate quantitative evaluation.

Incidentally, the invention of the present application is not restricted to the foregoing embodiments, and various modifications can be carried out without departing from its scope in the implementation steps. Moreover, the respective embodiments can be appropriately combined and carried out if possible, and advantages of the combination can be obtained in such a case. In addition, the foregoing embodiments include the present invention at various stages, and variety of inventions can be obtained by appropriate combinations under a plurality of disclosed structural conditions. For example, if several structural conditions are eliminated from all structural conditions disclosed in the embodiments, the problems described in the section "problems to be solved by the invention" can be raveled. When at least one of effects described in the section "effects of the invention" can be obtained, the structure from which these structural conditions are eliminated can be selected as the present invention.

According to the foregoing embodiments, it is possible to realize the ultrasonic diagnosis apparatus capable of accurately and effectively perform detection of a blood flow perfusion and quantitative evaluation of that perfusion even if a quantity of the contrast agent injected is large or a concentration of the same is high.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. An ultrasonic diagnostic apparatus comprising:
   a transmission/reception device which transmits for a plurality of times ultrasonic waves having an intensity capable of destructing a contrast agent to one scanning plane of an object to which the contrast agent has been injected and receives a reflected wave group from the object;
   a data generator which generates a plurality of accumulative addition data having different time phases based on at least one of a plurality of reflected waves constituting a plurality of continuous frames in the reflected wave group and generates subtraction data from a reflected wave received from the object with a predetermined timing; and
   an image information generator which generates calculated data having an operation value to which a plurality of the accumulative addition data has been accumulatively added and from which the subtraction data has been subtracted, and generates ultrasonic wave image information concerning the scanning plane based on the calculated data.

2. The ultrasonic diagnostic apparatus according to claim 1, wherein the subtraction data is generated from any one of a reflected wave received from the object before administration of the contrast agent, any one reflected wave other than a reflected wave received earliest in time among reflected waves composing the reflected wave group, and any one reflected wave other than a reflected wave received earliest in time among reflected waves composing a reflected wave group different from the reflected wave group.

3. The ultrasonic diagnostic apparatus according to claim 1, wherein said data generator performs the subtraction after multiplying the respective accumulative addition data by weighting coefficients having respective values.

4. The ultrasonic diagnostic apparatus according to claim 1, wherein when the operation value is negative, said data generator generates the calculated data with the operation value being determined as an absolute value or the operation value being determined as zero.

5. The ultrasonic diagnostic apparatus according to claim 1, wherein said data generator generates a time intensity curve based on the ultrasonic image information.

6. The ultrasonic diagnostic apparatus according to claim 1, further comprising a second data generator which generates second calculated data having an operation value to which a plurality of the accumulative addition data have been accumulatively added and from which a plurality of the frames of the subtraction data have been subtracted, and generates ultrasonic wave image information concerning the scanning plane based on the calculated data.

7. The ultrasonic diagnostic apparatus according to claim 1, wherein said transmission/reception device deepens focusing points of the ultrasonic waves gradually while transmitting for a plurality of number of times the ultrasonic waves.

8. An ultrasonic diagnostic apparatus comprising:
a transmission/reception device which transmits for a plurality of number of times ultrasonic waves having an intensity capable of destructing a contrast agent to one scanning plane of an object to which the contrast agent has been injected, and receives a reflected wave group from the object;
a data generator which generates a plurality of accumulative addition data having respective time phases based on at least one of a plurality of reflected waves composing a plurality of continuous frames in the reflected wave group, and generates subtraction data from a reflected wave received from the object with a predetermined timing;
a memory which stores therein a plurality of the accumulative addition data; and
an image information generator which generates calculated data obtained by subtracting the subtraction data from each of the accumulative addition data stored in said memory, and generates ultrasonic image information concerning the scanning plane based on the calculated data.

9. The ultrasonic diagnostic apparatus according to claim 8, wherein the subtraction data is generated from any one of a reflected wave received from the object before administration of the contrast agent, any one reflected wave other than a reflected wave received earliest in time among reflected waves composing the reflected wave group, and any one reflected wave other than a reflected wave received earliest in time among reflected waves composing a reflected wave group different from the reflected wave group.

10. The ultrasonic diagnostic apparatus according to claim 8, wherein said data generator performs the subtraction after multiplying the respective accumulative addition data by weighting coefficients having respect values.

11. The ultrasonic diagnostic apparatus according to claim 8, wherein when the operation value is negative, said data generator generates the calculated data with the operation value being determined as an absolute value or the operation value being determined as zero.

12. The ultrasonic diagnostic apparatus according to claim 8, wherein the data generator generates a time intensity curve based on the ultrasonic image information.

13. The ultrasonic diagnostic apparatus according to claim 8, further comprising a second data generator which generates second calculated data having an operation value to which a plurality of the accumulative addition data have been added and from which a plurality of the frames of the subtraction data have been subtracted, and generates ultrasonic image information concerning the scanning plane based on the second calculated data.

14. The ultrasonic diagnostic apparatus according to claim 8, wherein said transmission/reception device deepens focusing points of the ultrasonic waves gradually while transmitting for a plurality of number of times the ultrasonic waves.

15. An ultrasonic diagnostic apparatus control method comprising:
transmitting for a plurality of number of times ultrasonic waves having an intensity capable of destructing a contrast agent to one scanning plane of an object to which the contrast agent has been injected;
receiving a reflected wave group from the object;
generating a plurality of accumulative addition data having respective time phases based on at least one of a plurality of reflected waves composing a plurality of continuous frames in the reflected wave group;
generating subtraction data from a reflected wave received from the object with a predetermined timing;
generating calculated data having an operation value to which a plurality of the accumulative addition data have been added and from which the subtraction data has been subtracted; and
generating ultrasonic image information concerning the scanning plane based on the calculated data.

16. The ultrasonic diagnostic apparatus control method according to claim 15, wherein the subtraction data is generated from any one of a reflected wave received from the object before administration of the contrast agent, any one reflected wave other than a reflected wave received earliest in time among reflected waves composing the reflected wave group, and any one reflected wave other than a reflected wave received earliest in time among reflected waves composing a reflected wave group different from the reflected wave group.

17. The ultrasonic diagnostic apparatus control method according to claim 15, wherein generation of the accumulative addition data is executed by multiplying weighting coefficients having respective values in accordance with the respective accumulative addition data.

18. The ultrasonic diagnostic apparatus control method according to claim 15, wherein when the operation value is negative, the calculated data is generated with the operation value being determined as an absolute value or the operation value being determined as zero.

19. The ultrasonic diagnostic apparatus control method according to claim 15, further comprising generation of a time intensity curve based on the ultrasonic image information.

20. The ultrasonic diagnostic apparatus control method according to claim 15, further comprising:
generating second calculated data having an operation value to which a plurality of the accumulative addition data have been accumulatively added and from which a plurality of the frames of the subtraction data have been subtracted; and
generating ultrasonic image information concerning the scanning plane based on the second calculated data.

21. The ultrasonic diagnostic apparatus control method according to claim 15, wherein focusing points of the ultrasonic waves are deepened gradually while the ultrasonic waves are transmitted for a plurality of number of times.

22. An ultrasonic diagnostic apparatus control method comprising:
transmitting for a plurality of number of times ultrasonic waves having an intensity capable of destructing a contrast agent to one scanning plane of an object to which the contrast agent has been injected;
receiving a reflected wave group from the object;
generating a plurality of the accumulative addition data having different time phases based on at least one of a plurality of reflected waves composing a plurality of continuous frames in the reflected wave group;
generating subtraction data from a reflected wave received from the object with a predetermined timing;
generating calculated data obtained by subtracting the subtraction data from the each of accumulative addition data; and generating ultrasonic image information concerning the scanning plane based on the calculated data.

23. The ultrasonic diagnostic apparatus control method according to claim 22, wherein the subtraction data is generated from any one of a reflected wave received from the object before administration of the contrast agent, any one reflected wave other than a reflected wave received earliest in time among reflected waves composing the reflected wave group, and any one reflected wave other than a reflected wave received earliest in time among reflected waves composing a reflected wave group different from the reflected wave group.

24. The ultrasonic diagnostic apparatus control method according to claim 22, wherein generation of the accumulative addition data is executed by multiplying weighting coefficients having different values in accordance with the respective accumulative addition data.

25. The ultrasonic diagnostic apparatus control method according to claim 23, wherein when the operation value is negative, the calculated data is generated with the operation value being determined as an absolute value or the operation value being determined as zero.

26. The ultrasonic diagnostic apparatus control method according to claim 22, further comprising generation of a time intensity curve based on the ultrasonic image information.

27. The ultrasonic diagnostic apparatus control method according to claim 22, further comprising:

generating second calculated data having an operation value to which a plurality of the accumulative addition data have been added and from which a plurality of the frames of the subtraction data have been subtracted; and generating ultrasonic image information concerning the scanning plane based on the second calculated data.

28. The ultrasonic diagnostic apparatus control method according to claim 22, wherein focusing points of the ultrasonic waves are deepened gradually while the ultrasonic waves are transmitted for a plurality of number of times.

* * * * *